United States Patent
Schweizer

(10) Patent No.: US 9,402,390 B2
(45) Date of Patent: Aug. 2, 2016

(54) TISSUE RETRIEVAL, STORAGE, AND EXPLANT CULTURE DEVICE FOR THE DERIVATION OF STEM CELLS

(71) Applicant: Russell James Schweizer, Village of Lakewood, IL (US)

(72) Inventor: Russell James Schweizer, Village of Lakewood, IL (US)

( * ) Notice: Subject to any disclaimer, the term of this patent is extended or adjusted under 35 U.S.C. 154(b) by 0 days.

(21) Appl. No.: 14/949,127

(22) Filed: Nov. 23, 2015

(65) Prior Publication Data

US 2016/0073627 A1  Mar. 17, 2016

Related U.S. Application Data

(62) Division of application No. 13/782,021, filed on Mar. 1, 2013, now Pat. No. 9,192,157.

(60) Provisional application No. 61/605,725, filed on Mar. 1, 2012.

(51) Int. Cl.
*G01N 1/00* (2006.01)
*A01N 1/02* (2006.01)

(52) U.S. Cl.
CPC ............ *A01N 1/0268* (2013.01); *A01N 1/0273* (2013.01); *A01N 1/0284* (2013.01)

(58) Field of Classification Search
CPC ....................................................... G01N 1/10
See application file for complete search history.

(56) References Cited

U.S. PATENT DOCUMENTS

| 8,071,058 B2 | 12/2011 | Haywood et al. |
| 2007/0092412 A1 | 4/2007 | Haywood et al. |
| 2009/0238801 A1 | 9/2009 | Woodbury et al. |

FOREIGN PATENT DOCUMENTS

WO  2005102526 A1  11/2005

*Primary Examiner* — Jyoti Nagpaul
(74) *Attorney, Agent, or Firm* — Miller, Matthias & Hull LLP

(57) ABSTRACT

A device is provided for securing a tissue sample from biological material. The tissue sample is housed in bottom and top platens that are configured to promote fluid communication between the tissue sample and the exterior environment to permit transport or cryogenic fluid to contact the sample. Additionally, diskette assemblies may be provided within the platens that permit sub-samples to be separated without directly handling the tissue sample. The diskette assemblies may also be configured to promote fluid communication with the sub-sample housed therein.

20 Claims, 9 Drawing Sheets

TISSUE RETRIEVAL, STORAGE, AND EXPLANT CULTURE DEVICE FOR THE DERIVATION OF STEM CELLS

TECHNICAL FIELD

The present disclosure generally relates to methods and apparatus for obtaining tissue samples from biological materials.

BACKGROUND

Within the normal reproductive process, the gestation of a fetus within the female of the species typically occurs within a gestational sac. The gestational sac is comprised of a pair of juxtaposed membranes comprising an outer structure, such as the chorionic membrane (chorion) that forms an outer margin, and an inner structure, such as the amniotic membrane (amnion) which is closest proximity to the fetus. In childbirth following partuation of the gestational sac, commonly referred to as afterbirth, the membrane structure is typically disposed as medical waste. However, medical discoveries are increasingly finding valuable biomedical materials in the tissues of these materials, and specifically the amnion.

The first known clinical uses of the amnion began a century ago for the treatment of various wounds including burn trauma and skin ulcerations on the surface. Extended usage of the intact amnion and chorion tissue came in the 1950's with more focused procedures to treat skin burn sites. The value of amnion was exemplified in the 1960's with a proposal to establish an amnion bank.

Contemporary medicine has seen a relative explosion in the utility of the amnion tissue in the areas of treatment for ocular disorders and thermal and chemical burns. In these treatments, intact amnion tissue is literally transposed directly over the trauma or wound site and has been proven to promote faster healing and alleviate pain. Today the most prevalent use of amnion tissue is in surgical procedures involving the eye.

Recent research is shifting the primary focus of medical attributes to the area of stem cell derivation. The concept of "Regenerative Medicine", which is replacing, repairing and reconstructing diseased tissue and organs by stem cell therapies, is making rapid clinical progress. Multiple stem cell populations have been identified in the amnion and chorion. When derived at child birth, the benefits can be greater because of their pristine nature due to a lack of exposure to environmental toxins. Any or all derived stem cells may have future clinical utility and may play an extremely large and beneficial role in regenerative medicine.

An alternate and proven method of stem cell derivation in current practice today, and also practiced for the benefit of regenerative medicine, is that of harvesting the placental umbilical cord blood. By this practice, a single sample of blood is harvested from the umbilical cord at birth. The harvested blood is then processed to derive the appropriate beneficial stem cells and the sample is frozen for future use. The ability to cryogenically freeze living cells for thawing and renewal at a later time is a well proven and common practice for many biological materials and is commonly used for procedures such as in vitro fertilization of embryos implanted to induce pregnancy. Cord blood, amnion and chorion tissues are likewise proven biological materials that are conducive to being frozen for an unlimited time. The stem cells derived from cord blood are typically most appropriate for the treatment of hematopoietic (i.e., blood-related) illnesses, and the singular sample retrieved will typically be saved for the future benefit of the donor. By contrast, it has been found that amnion derived stem cells possess qualities that become quite beneficial for treatment of illnesses other than hematopoietic, such as skeletal and cardiovascular. Fundamentally, umbilical cord blood produces hematopoietic stem cells and amnion and chorion produce mesenchymal and epithelial stem cells, all of which are of growing benefit to the healthcare practice of regenerative medicine and are capable of being harvested and preserved for future benefit.

With the growing number of possible clinical applications for amnion and chorion, the devices and methods used to retrieve and preserve these tissues are of increasing interest to the health care community. As new procedures are developed, the devices must be adapted and may advantageously facilitate, optimize, and simplify retrieval and storage of amnion and chorion directly from the afterbirth.

SUMMARY OF THE DISCLOSURE

Devices and methods are disclosed for isolating biological materials and placing them in a position highly conducive to long term storage, thereby preserving the materials intact and preserving them for use by future generations. The benefits of banking and preserving these materials to aid in future medical procedures will only increase in time due to the technological advances in the healthcare industry.

According to some aspects of this disclosure, a device is provided for retrieving, capturing, transporting, and cryogenically storing tissue samples from biological material. In some applications, the device may be used to harvest and store amnion or chorion tissue samples.

Efficient retrieval and handling of amnion and chorion membranes is complicated by the physical characteristics of the membranes. The amnion and chorion membranes are typically extremely thin, possess a level of tensile attributes, but also exhibit a notch sensitive behavior which makes the membranes susceptible to tearing and subsequent curling up upon itself if not properly handled. Tearing and curling of the membranes can destroy cellular viability, and therefore may be deleterious to future clinical value.

Additionally, the amnion and chorion are living membranes when harvested at childbirth, and therefore they should be handled, transported, and preserved correctly to maximize the yield of living cells that are obtained and preserved for future use. Therefore, in addition to folding, or curling back upon itself, or any act whereby the tissue surface is touched by itself, or other capturing elements causing harmful effects, similar damage can be caused by allowing the membrane surface to dry.

In view of the foregoing, according to certain aspects of this disclosure a device may be provided having a working platform upon which to secure the membrane in a way that spreads it out straight, flat and secure. At birth, the amnion and chorion are intimately attached and therefore may require manual separation. In some embodiments, therefore, the methods and devices may secure a leading edge of one membrane (such as the amnion) on a platen while the membranes are separated. After separation, the entire amnion sample may remain on the platen.

The methods and devices disclosed herein may also create multiple smaller sub-samples from a single, larger sample. For example, a first or bottom platen assembly may be capable of being reconfigured into multiple sub-platen assemblies, so that a large sample provided on the bottom platen can be simply and efficiently separated into multiple sub-samples disposed on sub-platen assemblies. Generating multiple sub-samples from a single sample typically requires cutting or tearing of the tissue while simultaneously stabilizing the assembly so that it does not contract or curl upon itself. Accordingly, the methods and devices disclosed herein may include a second or top platen assembly configured to retain the straight and flat nature of each individual sub-sample both prior to and after separation. The top platen assembly is positioned over the bottom platen assembly, and guides are provided to consistently and accurately locate and mates the top and bottom platens with the tissue disposed therebetween, all while facilitating separation into multiple sub-assemblies carrying sub-samples at a later time, such as prior to cryogenic storage.

According to additional aspects of the present disclosure, the methods and devices disclosed herein may further provide a liquid containment of the mated top and bottom platens to preserve the sample as it is transported to a cryogenic storage facility intact.

Therefore, all means of capturing the flat sheet of tissue is accomplished by interrupted and circuitous surfaces that facilitate the flow and intimate contact of a transport liquid with the membrane top and bottom surfaces within a leak proof container device.

According to further aspects of the present disclosure, the methods and devices disclosed herein may enable removal of the mated top and bottom platen assembly from a transport containment, and permit easy separation of the larger tissue sample into multiple, individual, smaller sub-samples. To that end, each sub-sample may be secured in a manner that retains the flatness of the samples. In some embodiments, diskette assemblies may be provided for securing sub-samples, with each diskette assembly including a top diskette and a bottom diskette. Individual top diskettes may be mechanically coupled to the top platen, while individual bottom diskettes may be mechanically coupled to the bottom platen. In order to create multiple individual and smaller samples from a single large sample, the mated platen assembly may be removed from the transport container and placed on a flat surface. The multiple top diskettes, which protrude from the top platen, may be pushed downward and seated into the bottom platen and respective bottom diskettes. When all top diskettes are seated in their respective bottom diskettes, the top platen may be lifted and removed from the assembly. The array of multiple diskette assemblies may remain loosely attached in the exposed bottom platen. Each diskette assembly may encompass an associated portion of the tissue sample, while some or all to the diskette assemblies may continue to be adjoined by connecting membrane of the sample. A gap may be provided between adjacent diskette assemblies that permits a cutting tool, such as a scalpel, to be inserted to cut the connecting membrane. Alternatively, the diskette assemblies may be manually removed from the bottom platen in such a way to tear the connecting membrane and free each individual diskette assembly while the associated sub-sample contained within the separated diskette assembly remains secure and intact.

According to additional aspects of the present disclosure, each diskette may be placed into a vial for cryogenic storage. A cryogenic preservative solution can be added to the vial, while the diskette assemblies limit surface contact with the membrane, retain membrane flatness, and allow maximum solution intimacy with all surfaces for optimal preservation.

In some embodiments, one of the top and bottom diskettes may incorporate a sharp cutting element configured to cut through the sub-sample as the top diskette is mechanically seated on the bottom diskette.

BRIEF DESCRIPTION OF THE DRAWINGS

Those of skill in the art will understand that the drawings portrayed and described are for illustration purposes only and not intended to limit the scope of the invention.

DETAILED DESCRIPTION

The methods and devices disclosed herein enable the successful retrieval of a large tissue sample from biological material in a sterile hospital environment. The tissue sample is captured with limited trauma and degradation to the material while encapsulating it for further transfer and ultimate preservation while in a living state. In particular, the methods and devices disclosed herein may be used to retrieve and preserve amnion tissue that is presented only during the birth of the species. A sample of living amnion tissue is deemed to comprise a highly beneficial population of stem cells, and can therefore be frozen in time to preserve cell viability for later utilization. The methods and devices disclosed herein may also facilitate cryogenic storage and return to maximum living cell viability.

Figure 1:
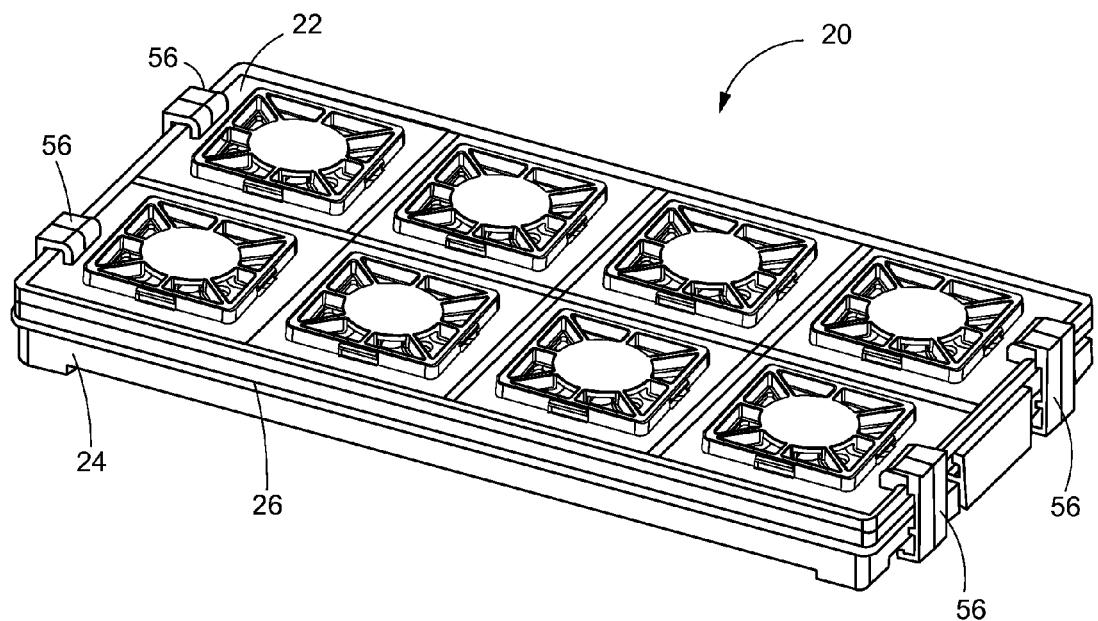
FIG. 1 is a perspective view of a device for securing a tissue sample constructed according to the present disclosure.

Referring now to the drawings, FIG. 1 illustrates an embodiment of a tissue securing device 20. The issue securing device 20 may include a bottom platen 22 and a top platen 24. The bottom and top platens 22, 24 may be provided as separate assemblies so that biological material may be positioned between the platens. Accordingly, when the top platen 24 is joined to the bottom platen 22, a tissue sample 26 may be secured by the assembly, as described in greater detail below.

Figure 2:
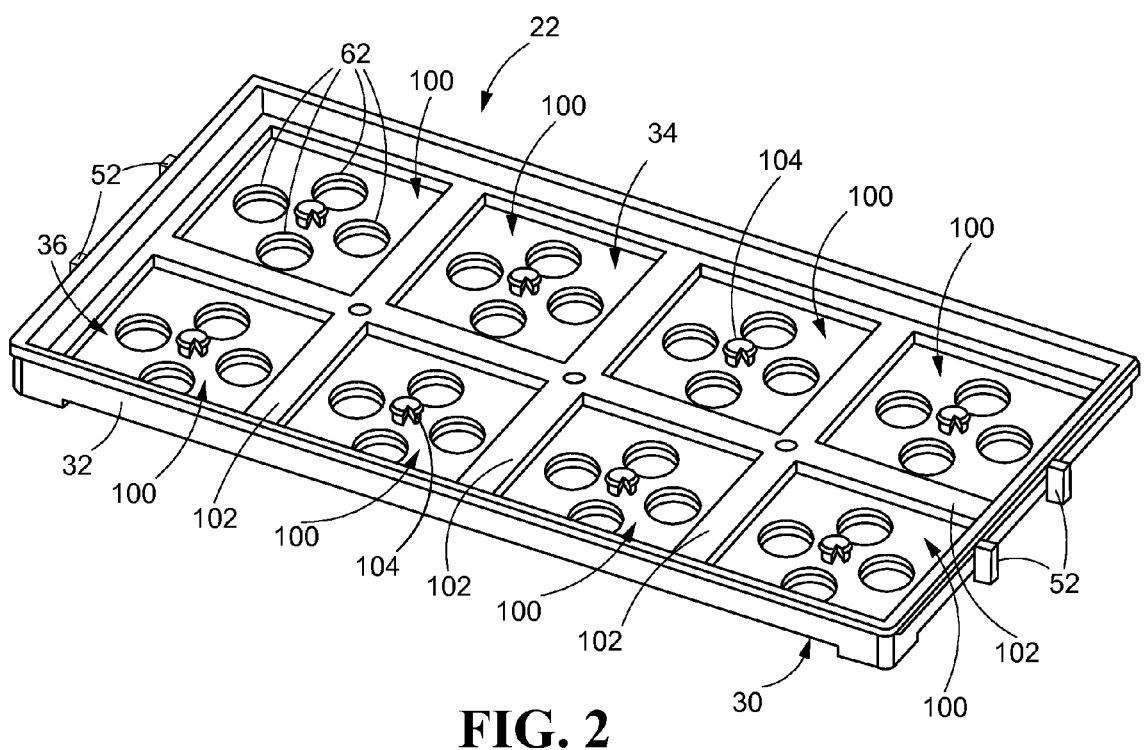
FIG. 2 is a perspective view of a bottom platen used in the device of FIG. 1.
Figure 3:
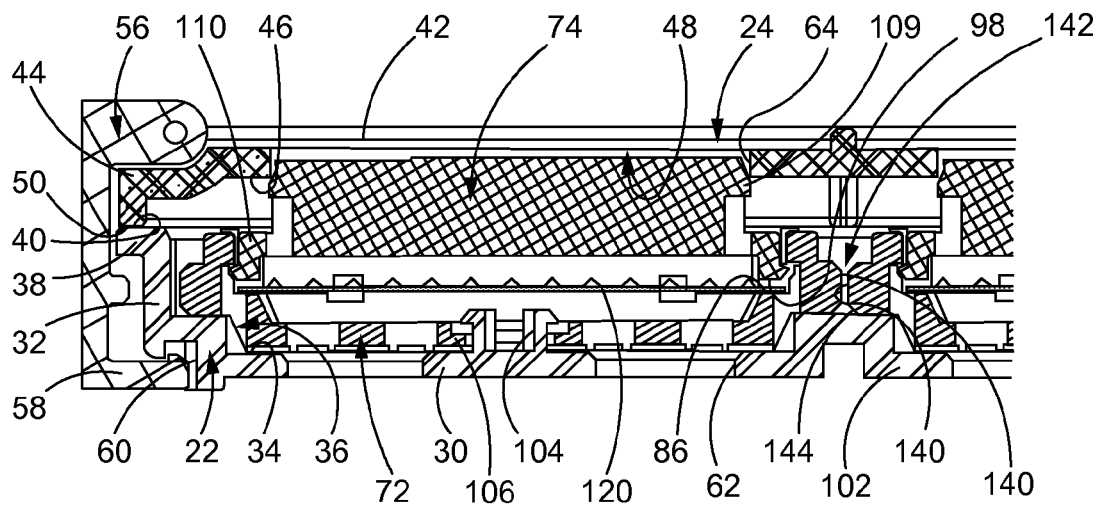
FIG. 3 is a partial side elevation view, in cross-section, of the device of FIG. 1 showing a diskette assembly in an actuated position.

The bottom platen 22 is shown in FIG. 2 as having a generally tray-like appearance formed by a bottom platen base 30 and a bottom platen side wall 32. The bottom platen base 30 defines a bottom platen base inner surface 34, while the bottom platen side wall 32 extends upwardly from a perimeter of the bottom platen base 30. Together, the bottom platen side wall 32 and bottom platen base 30 define a bottom platen base receptacle 36. As best shown in FIG. 3, a flange 38 coupled to a top end of the bottom platen side wall 32 may define a bottom platen engagement surface 40. The bottom platen engagement surface 40 may extend around a perimeter of the bottom platen base receptacle 36, thereby to provide a first surface for securing the outer edge of the tissue sample 26. The bottom platen engagement surface 40 is spaced from the bottom platen base inner surface 34 to limit the amount of structure in direct contact with the tissue sample 26. To provide a stable surface on which the biological material may be placed, the bottom platen engagement surface 40 may be substantially planar.

Figure 4:
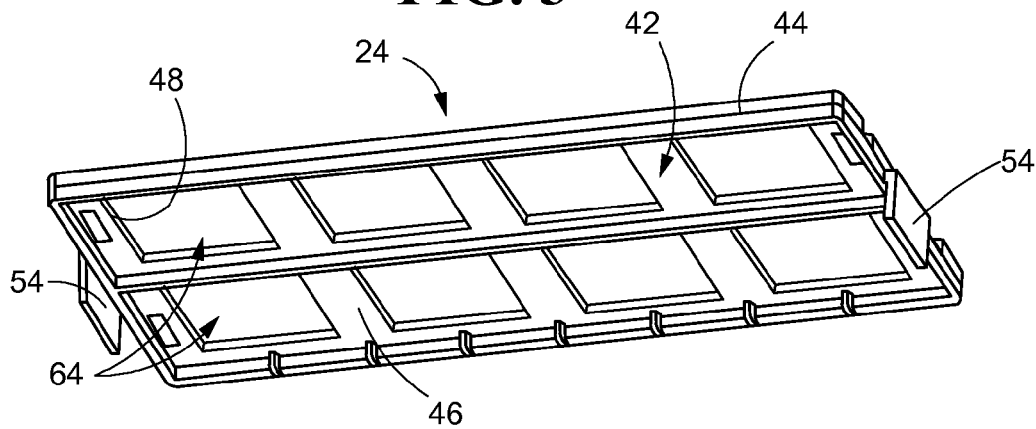
FIG. 4 is a perspective view of a top platen used in the device of FIG. 1.

Turning to FIG. 4, the top platen 24 is illustrated as having a generally inverted, tray-like appearance formed by a top platen cover 42 and a top platen side wall 44. The top platen cover 42 defines a top platen cover inner surface 46, while the top platen side wall 44 extends downwardly from a perimeter of the top platen cover 42. Together, the top platen side wall 44 and top platen cover 42 define a top platen cover receptacle 48. As best shown in FIG. 3, a bottom portion of the top platen side wall 44 defines a top platen engagement surface 50. The top platen engagement surface 50 extends around a perimeter of the top platen cover receptacle 48, thereby to provide a second surface for securing the outer edge of the tissue sample 26. The top platen engagement surface 50 is spaced from the top platen cover inner surface 46 to again limit direct contact with the tissue sample 26.

The top platen engagement surface 50 is shaped to cooperatively interact with the bottom platen engagement surface 40. As used herein, the term "cooperatively interact" means that the recited structures are configured so that they can be positioned in a tissue engaging position, thereby to secure the tissue sample 26 between the two engagement surfaces. Accordingly, in some embodiments, the top platen engagement surface 50 may have a shape that is a mirror image of that of the bottom platen engagement surface 40, so that the engagement surfaces 40, 50 can be directly aligned. In these embodiments, the engagement surfaces 40, 50 may be configured to directly abut one another, or they may be configured to be spaced by a distance that is sufficiently small to firmly secure the tissue sample 26 therebetween. Alternatively, the engagement surfaces 40, 50 may be configured to have a closely telescoping fit, thereby to pinch an outer edge of the tissue sample 26 therebetween. The engagement surfaces 40, 50 may be configured to sever, shear, or otherwise separate an outer periphery of the biological material to obtain the final shape of the tissue sample 26. Alternatively, the engagement surfaces may simply secure the tissue sample and a separate cutting step may be performed to remove the excess periphery of the biological material.

The bottom and top platens 22, 24 may be provided as separate components that can be assembled to secure the tissue sample 26. To assist with assembly, the bottom and top platens 22, 24 may include alignment components so that the top platen engagement surface 50 is positioned properly with respect to the bottom platen engagement surface 40. As shown in FIG. 2, the bottom platen 22 may include a first alignment structure, such as two pairs of brackets 52 extending outwardly from opposite ends of the bottom platen side wall 32, while the top platen 24 may include a second alignment structure, such as two tabs 54 extending downwardly from opposite ends of the top platen side wall 44 that are sized for insertion between the two pairs of brackets 52. The bracket pairs 52 and tabs 54 are located such that when the tabs 54 are inserted into the respective bracket pairs 52, the top platen engagement surface 50 will be properly positioned relative to the bottom platen engagement surface 40, thereby permitting cooperative interaction therebetween.

The tissue securing device 20 may further include a coupler assembly configured to releasably couple the bottom and top platens 22, 24. As best shown with reference to FIGS. 1 and 3, the coupler assembly may include a latch 56 having a base rotatably coupled to the top platen 24 and a hook end 58. Additionally, the bottom platen 22 may be formed with a coupler recess 60 configured to releasably engage the hook end 58 of the latch 56. Accordingly, when the top platen 24 is assembled on top of the bottom platen 22, the latch 56 may be rotated until the hook end 58 engages the coupler recess 60, thereby to firmly secure the top platen 24 to the bottom platen 22. As the coupler assembly is locked in place, the top platen 24 may be further pulled toward the bottom platen 22, driving the top platen engagement surface 50 toward the bottom platen engagement surface 40 and further securing the periphery of the tissue sample 26.

The tissue securing device 20 may be configured to promote exposure of the tissue sample 26 to controlled exterior environments, such as transport fluid or cryogenic media. As best shown in FIGS. 2 and 3, the bottom platen base 30 defines a plurality of bottom platen base apertures 62 that fluidly communicating between an exterior of the bottom platen 22 and the bottom platen base receptacle 36. Additionally, as best shown in FIGS. 3 and 4, the top platen cover 42 defines a plurality of top platen cover apertures 64 fluidly communicating between an exterior of the top platen 24 and the top platen cover receptacle 48. The bottom platen base apertures 62 and top platen cover apertures 64 promote fluid communication from an exterior of the securing device 20 and the tissue sample 26, which can be beneficial when the device 20 is submerged in transport fluid or exposed to cryogenic media.

Figure 5:
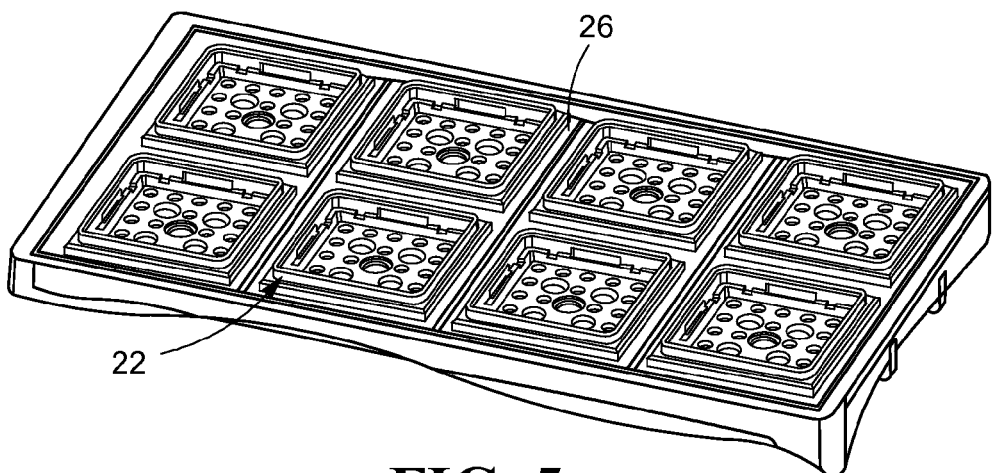
FIG. 5 is a perspective view of a bottom portion of the device for securing a tissue sample with biological material extending there over.
Figure 6:
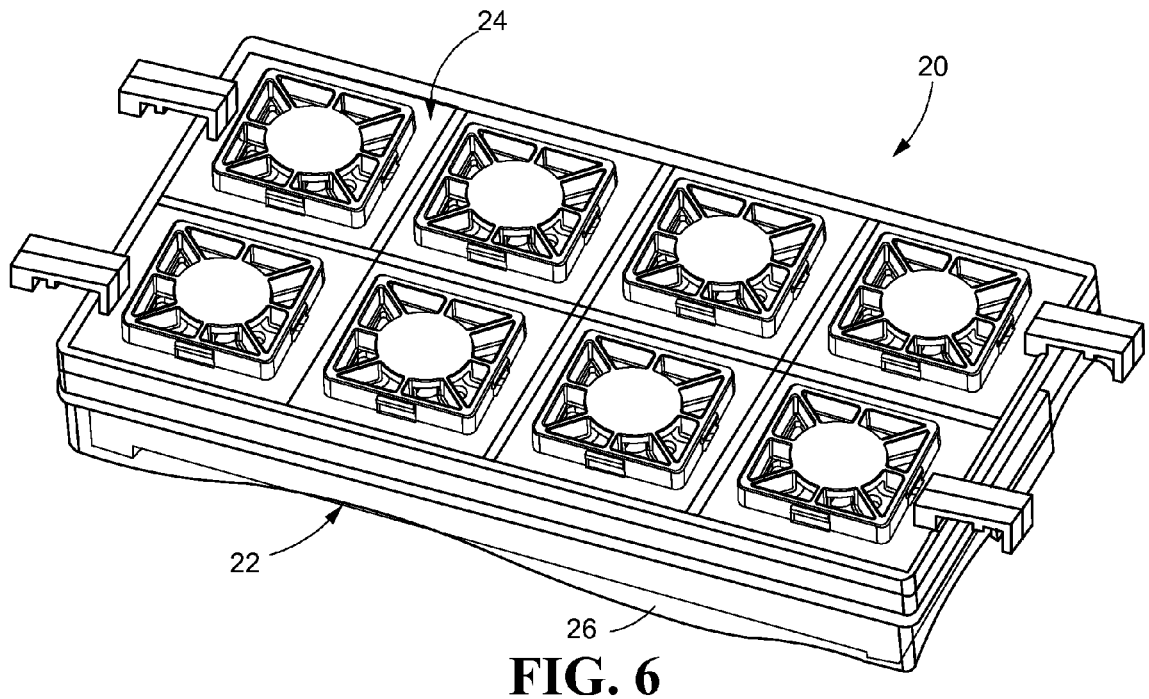
FIG. 6 is a perspective view showing a top platen positioned over the bottom platen with biological material disposed therebetween.
Figure 7:
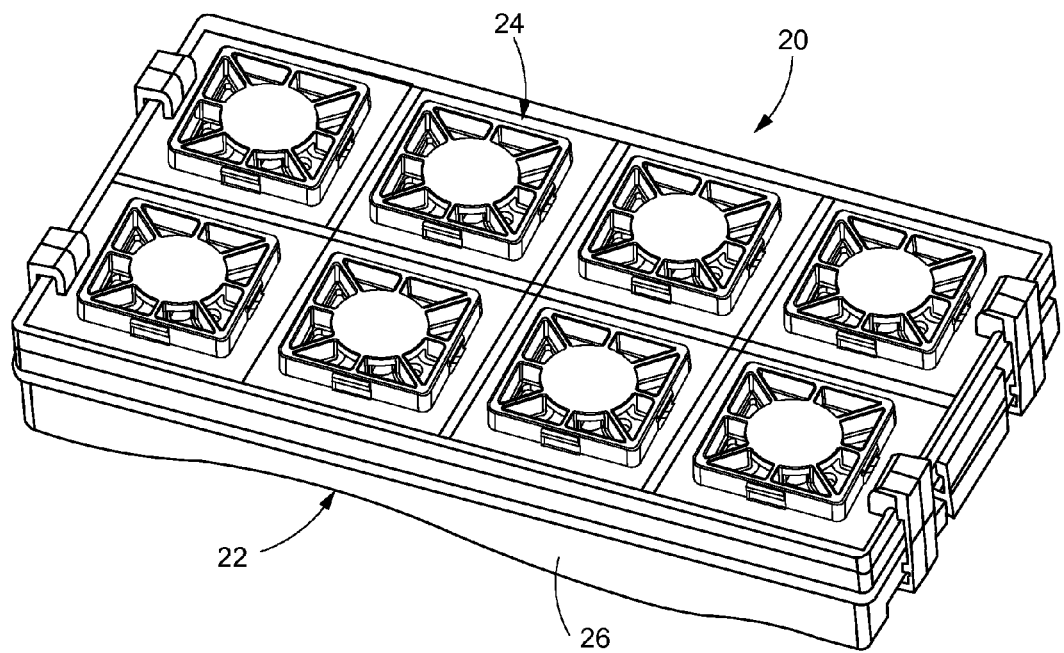
FIG. 7 is a perspective view of the device with the top platen secured to the bottom platen.

The bottom and top platens 22, 24 of the securing device 20 may be used on their own to obtain a relatively large tissue sample 26. In operation, the top platen 24 is initially separated from the bottom platen 22. Biological material may be placed over the bottom platen 22 so that an outer periphery of the biological material drapes over the sides of the bottom platen 22 (FIG. 5). Using the alignment components, the top platen 24 may be assembled onto the bottom platen 22 until the top platen engagement surface 50 is properly positioned relative to the bottom platen engagement surface 40 (FIG. 6). Next, the coupler assembly may be engaged to lock the top platen 24 onto the bottom platen 22 (FIG. 7). During this process, the top platen engagement surface 50 is moved into a tissue engaging position relative to the bottom platen engagement surface 40, so that a perimeter portion of what is to be the tissue sample 26 is firmly secured therebetween. The excess periphery of biological material is removed either automatically or in a separate cutting process, thereby to obtain the final shape of the tissue sample 26 (FIG. 1).

Figure 8:
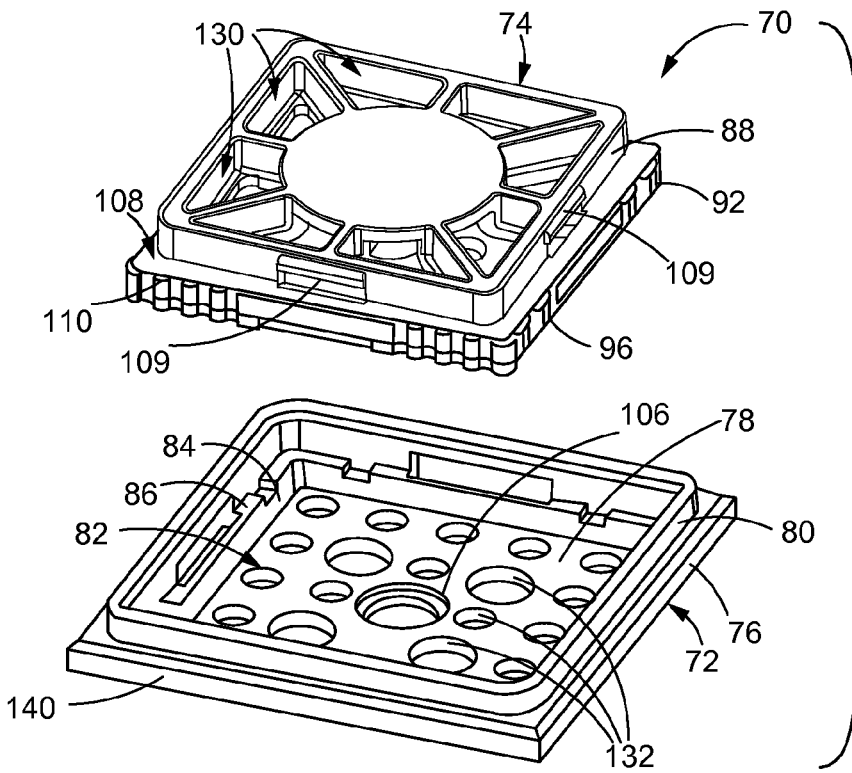
FIG. 8 is an exploded top perspective view of a diskette assembly.
Figure 9:
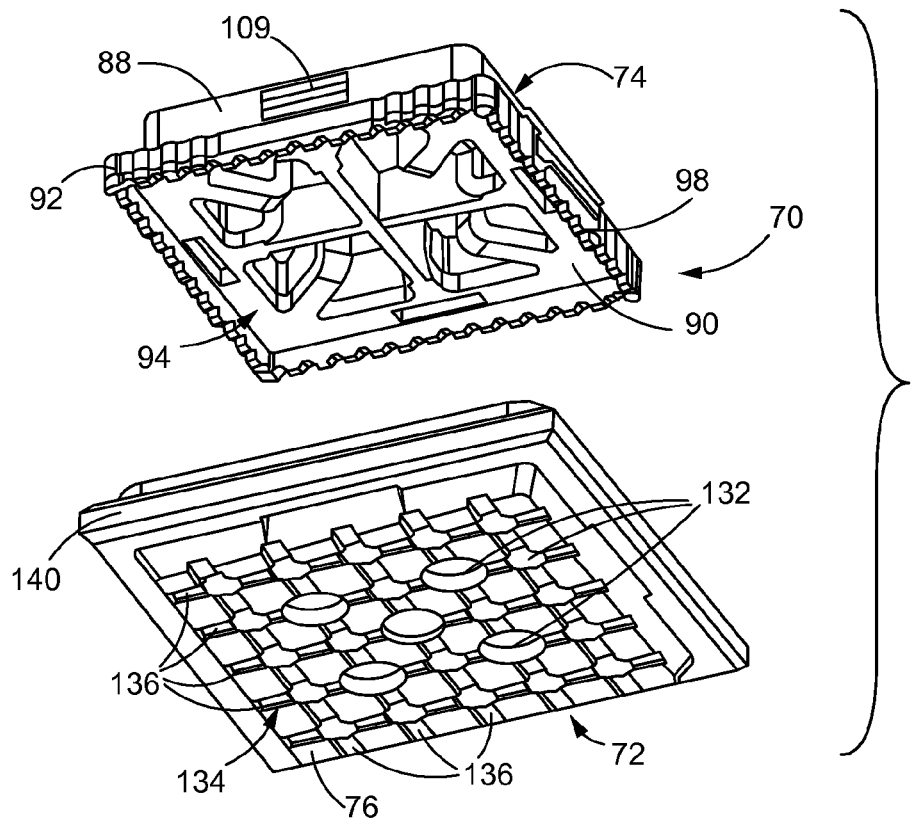
FIG. 9 is an exploded bottom perspective view of the diskette assembly of FIG. 8.

While the bottom and top platens 22, 24 have separate utility, the securing device 20 may further include an array of diskette assemblies 70 for separating the tissue sample 26 into multiple, smaller sub-samples. Each diskette assembly 70 may include a diskette lower housing 72 and a diskette upper housing 74, as best shown in FIGS. 8 and 9.

The diskette lower housing 72 may include a lower housing base 76 defining a lower housing base inner surface 78. A lower housing side wall 80 extends upwardly from the lower housing base 76 so that the lower housing base 76 and the lower housing side wall 80 define a lower housing receptacle 82. A lower housing shoulder 84 projects inwardly from the lower housing side wall 80 to define a lower housing engagement surface 86. The lower housing engagement surface 86 extends around a perimeter of the lower housing receptacle 82 and is spaced a distance above the lower housing base inner surface 78.

The diskette upper housing 74 may include an upper housing cover 88 defining an upper housing cover inner surface 90. An upper housing side wall 92 extends downwardly from the upper housing cover 88 so that the upper housing side wall 92 and upper housing cover 88 define an upper housing receptacle 94. The upper housing side wall 92 has a lower edge 96 defining an upper housing engagement surface 98. The upper housing engagement surface 98 extends around a perimeter of the upper housing receptacle 94 and is spaced a distance below the upper housing cover inner surface 90. The upper housing engagement surface 98 may be shaped to cooperatively interact with the lower housing engagement surface 86, similar to the engagement surfaces 40, 50 described above.

Figure 10:
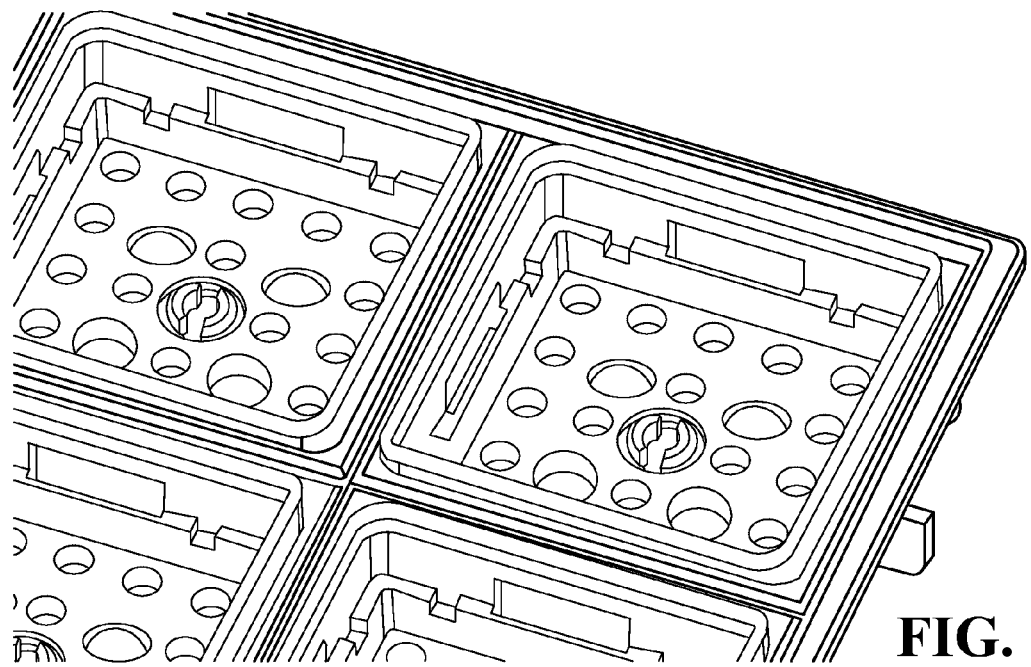
FIG. 10 is a perspective view of a bottom platen with attached diskette lower housings.
Figure 11:
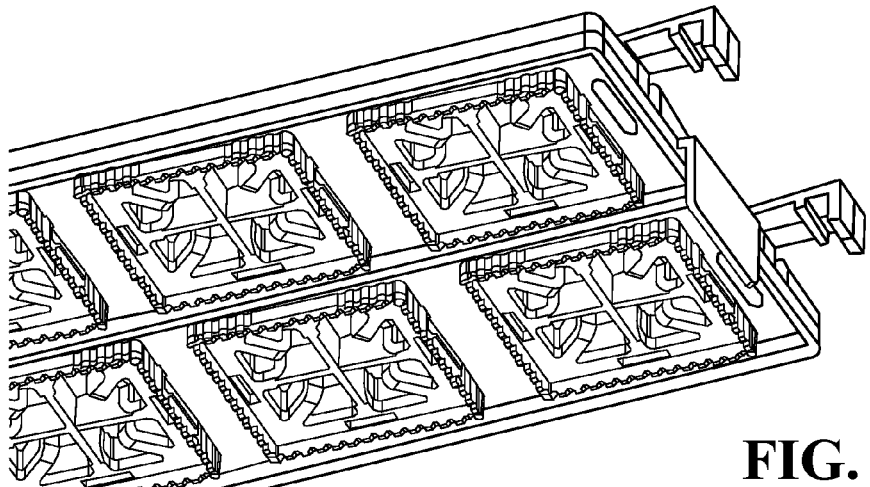
FIG. 11 is a perspective view of a top platen with attached diskette upper housings.

The bottom platen 22 may be configured to secure the diskette lower housings 72 in defined locations to facilitate registration of each diskette lower housing 72 with an associated diskette upper housing 74. As best shown in FIG. 1, the bottom platen base inner surface 34 defines an array of bottom platen base recesses 100, each of which is sized to receive a diskette lower housing 72. The bottom platen base recesses 100 may be formed by a series of intersecting platforms 102 that are elevated from the bottom platen base inner surface 34, but not as high as the bottom platen engagement surface 40. A base retainer 104 may extend upwardly from the bottom platen base inner surface 34 into each bottom platen base recess 100 and may be configured to releasably attach to a retainer aperture 106 formed in the diskette lower housing 72, as best shown in FIG. 10.

Similarly, the top platen 24 may be configured to secure the diskette upper housings 74 in defined locations to facilitate registration with an associated diskette lower housing 72. As best shown in FIG. 4, the top platen cover defines an array of cover apertures 64. Each upper housing cover 88 is sized for insertion through the cover apertures 64. An upper housing shoulder 108 (FIG. 8) extends outwardly from the upper housing cover 88 and defines a shoulder surface 110 configured to engage the top platen cover inner surface 46, thereby to prevent further insertion of the diskette upper housing 74 through the cover aperture 64. A flexible cover tab 109 may project outwardly from the upper housing cover 88 that may deflect to pass through the cover aperture 64. Once the cover tab 109 is clear of the cover aperture 64, it may resume its original shape, thereby by to secure the diskette upper housing 74 in a normal position. Subsequently, when sufficient downward force is applied to the upper housing cover 88, the cover tab 109 may again deflect to permit the diskette upper housing 74 to move downwardly to an actuated position, as discussed in greater detail below.

Each cover aperture 64 is positioned to register with an associated bottom platen base recess 100, so that each associated cover aperture 64 and bottom platen base recess 100 define a diskette receptacle configured to ultimately receive and enclose a diskette assembly 70. For example, bottom platen base recesses 100 and cover apertures 64 may be located relative to the alignment components of the bottom and top platens 22, 24, respectively, such that when the alignment components are engaged to assemble the bottom and top platens 22, 24, the lower and upper housing engagement surfaces 86, 98 are simultaneously aligned.

Figure 12:
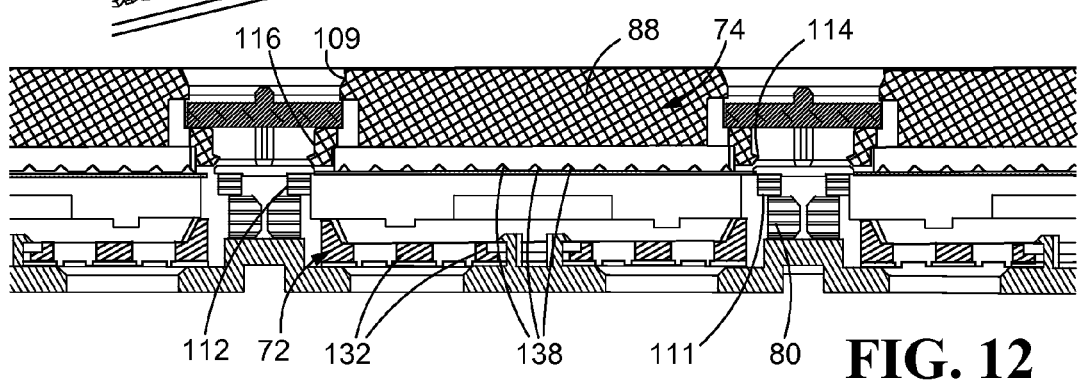
FIG. 12 is a side elevation view, in cross-section, of the device of FIG. 1 showing diskettes in the normal position.

Each diskette assembly 70 may be configured so that the diskette lower housing 72 automatically engages the diskette upper housing 74 during operation, such as when the diskette upper housing 74 is dislodged from the top platen 24 and moved to the actuated position. For example, as best shown in FIG. 12, the diskette lower housing 72 may include a lower housing retainer in the form of a lower housing flange 111 flange extending inwardly from the lower housing side wall 80 and defining a lower housing flange surface 112. The diskette upper housing 74 may include an upper housing retainer in the form of a flexible tab 114 protruding outwardly from the upper housing side wall 92 and defining an upper tab surface 116. As the diskette upper housing 74 is driven toward the diskette lower housing 72, the tab 114 may deflect until it passes the lower housing flange 111, at which time the tab 114 may resume its original shape. In this position, the upper tab surface 116 will engage the lower housing flange surface 112 to resist separation of the diskette upper housing 74 from the diskette lower housing 72.

Movement of the diskette upper housing 74 from the normal position to the actuated position may facilitate separating one or more sub-samples 120 from the tissue sample 26. In the normal position, where the diskette upper housing 74 engages the top platen 22, the upper housing engagement surface 98 is positioned above the top platen engagement surface 50 and is aligned with but spaced from the lower housing engagement surface 86, as shown in FIG. 12. In the actuated position, the diskette upper housing 74 is disengaged from the top platen 22 and moved downwardly so that the upper housing engagement surface 98 is positioned below the top platen engagement surface 50, as best shown in FIG. 3. When in the actuated position, the upper housing engagement surface 98 may be in a tissue engaging position such that a periphery of the sub-sample 120 is pinched between the lower and upper housing engagement surfaces 86, 98 (FIG. 3). The engagement surfaces 86, 98 may abut or may be spaced by a distance sufficiently small so that the sub-sample 120 is secured therebetween. In some embodiments, the lower and upper housing side walls 80, 92 may be configured to shear, cut, or otherwise sever through the tissue sample 26.

Each diskette assembly 70 may be configured to promote fluid communication from the exterior environment to an interior space surrounding the tissue sub-sample 120. As best shown in FIGS. 8-12, each upper housing cover 88 defines a plurality of upper housing cover passages 130 fluidly communicating between an exterior of the upper housing cover 88 and the upper housing receptacle 94. Additionally, each lower housing base 76 defines a plurality of lower housing base apertures 132 fluidly communicating between an exterior of the lower housing base 76 and the lower housing receptacle 82. A bottom surface 134 of the diskette lower housing 72 may further be formed with channels 136 extending between each of the lower housing base apertures 132, thereby to further promote fluid flow into the lower housing receptacle 82. Additionally, the upper housing engagement surface 98 may be configured to promote additional fluid flow to the sub-sample 120. More specifically, the upper housing engagement surface 98 may be formed with a series of upper housing engagement surface passages 138 (FIG. 12) that fluidly communicate between an exterior of the diskette upper housing 74 and the upper housing receptacle 94.

Figure 13:
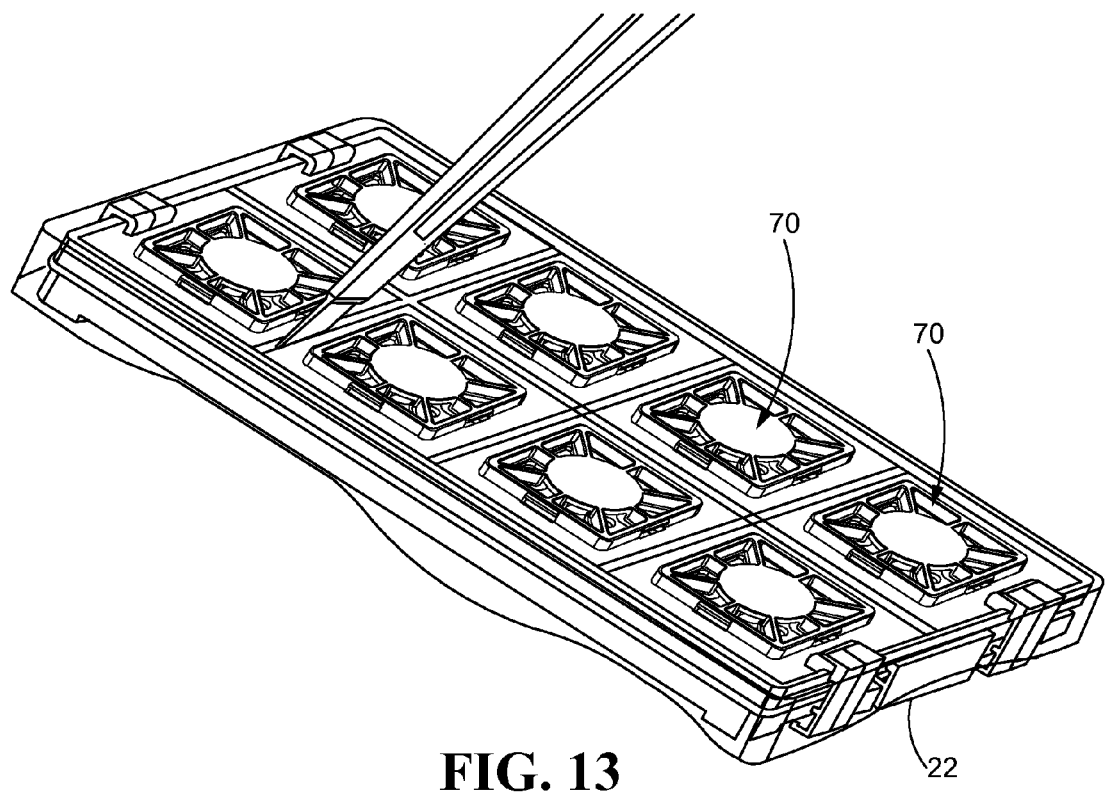
FIG. 13 is a perspective view showing the device with the top platen removed and a scalpel cutting between adjacent diskettes, thereby to obtain sub-samples from the tissue sample.
Figure 14:
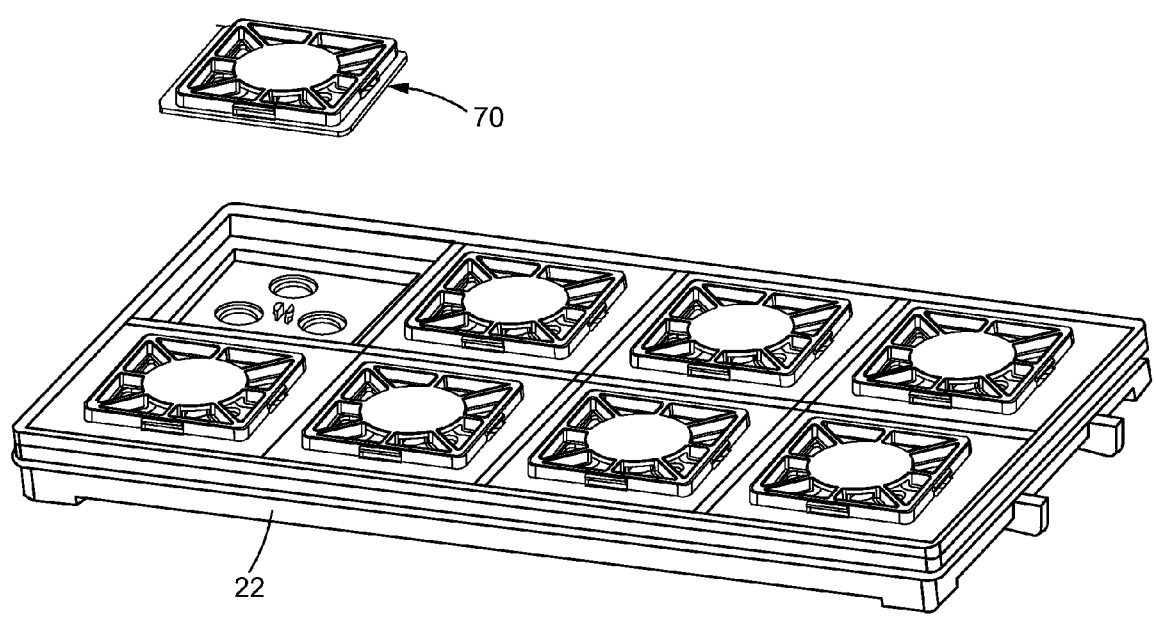
FIG. 14 is a perspective view of the bottom platen with a diskette assembly removed for transport or storage.

In some embodiments, the device 20 may be configured to facilitate a separate cutting step to separate the sub-sample 120. In these embodiments, the sub-sample 120 is not separated simultaneously as the diskette upper housing 74 is moved to the actuated position. Instead, movement of the diskette upper housing 74 only secures a periphery of the sub-sample 120 between the lower and upper housing engagement surfaces 86, 98. A separate cutting step may be facilitated by sufficiently spacing the bottom platen base recesses 100 so that a cutting gap 142 is provided between lower housing side wall peripheries 140 of adjacent diskette lower housings 74 (FIG. 3). The platforms 102 may extend between the adjacent bottom platen base recesses 100, and therefore an upper platform surface 144 may be aligned with the cutting gap 142 to provide stop for the cutting blade, as shown in FIG. 13. An individual diskette assembly 70 holding a sub-sample 120 may then be separated from the bottom platen 22, as shown in FIG. 14.

Figure 15:
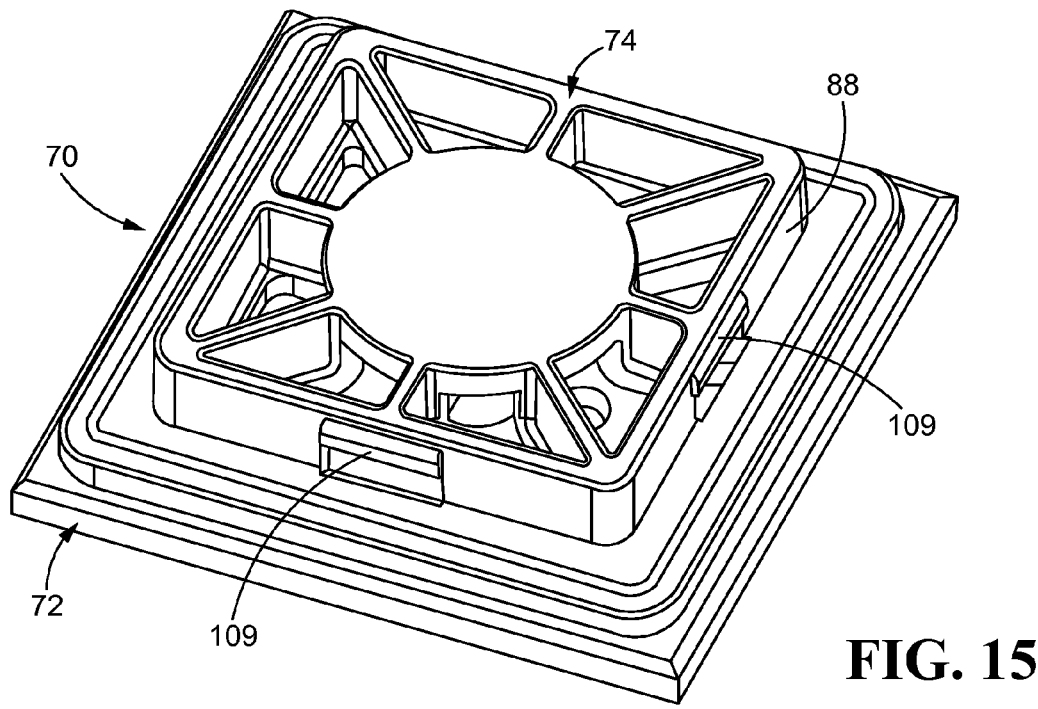
FIG. 15 is a perspective view of a diskette assembly.
Figure 16:
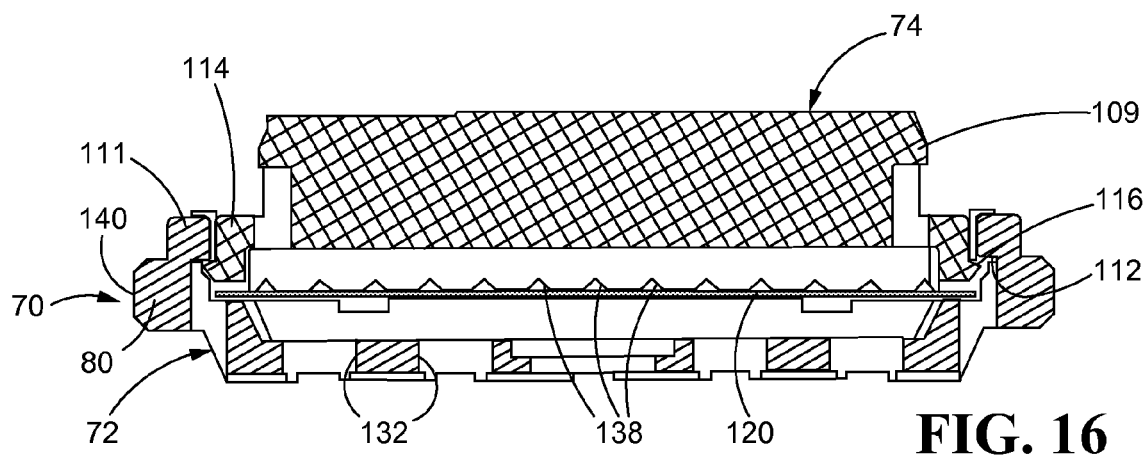
FIG. 16 is a side elevation view, in cross-section, of the diskette assembly of FIG. 15.
Figure 17:
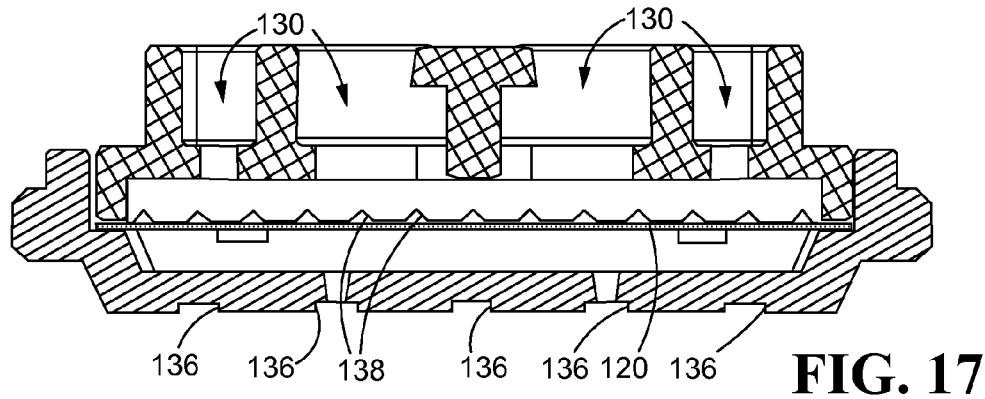
FIG. 17 is a side elevation view, in cross-section, of the diskette assembly of FIG. 15.

A diskette assembly 70 having engaged diskette lower and upper housings 72, 74 is illustrated in FIGS. 15-17. From these drawings it will be appreciated that a periphery of the sub-sample 120 is secured within the housings 72, 74 with minimal direct contact. Additionally, it is seen how the upper housing cover passages 130, lower housing base apertures 132, channels 136, and upper housing engagement surface passages 138 promote fluid communication between an exterior of the diskette assembly 70 and the sub-sample 120.

Figure 18:
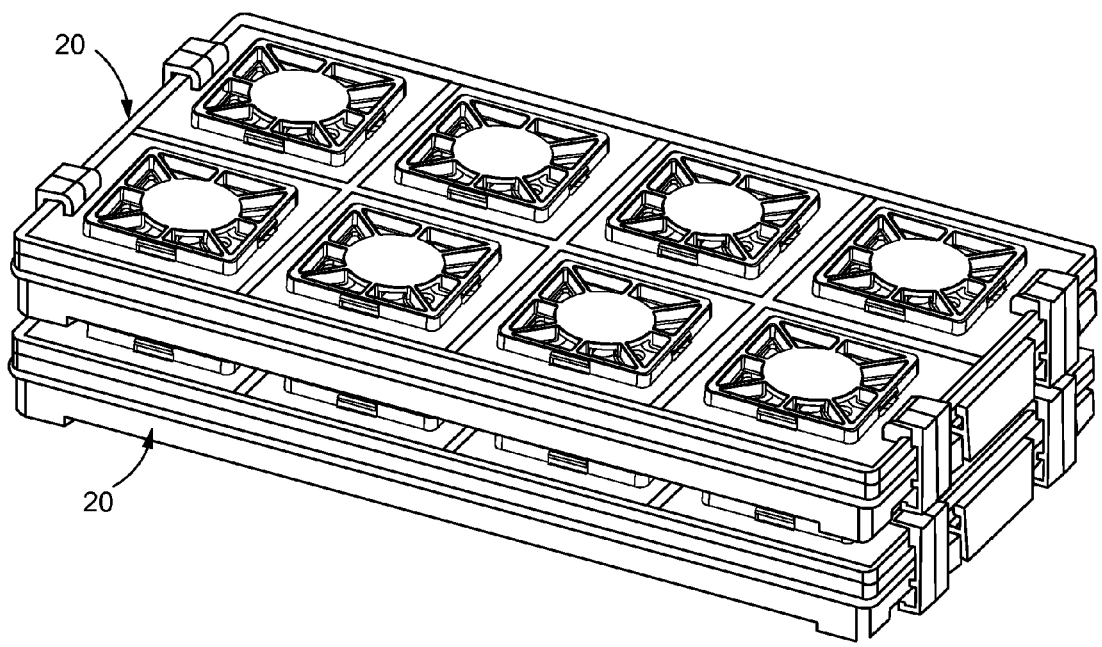
FIG. 18 is a perspective view of two devices for securing tissue samples in a nested stack configuration.
Figure 19:
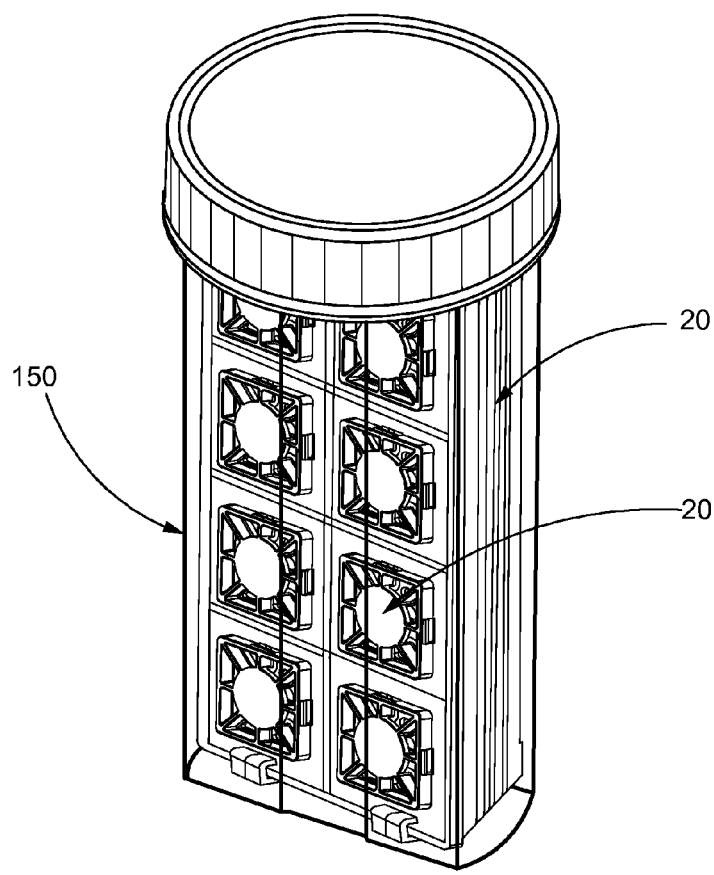
FIG. 19 is a perspective view of the two stacked devices of FIG. 18 inserted into a transport vial.

FIG. 18 illustrates two devices 20 stacked in a nested configuration. The stacked devices 20 may be inserted into a transport vessel 150 as shown in FIG. 19. The transport vessel 150 may be filled with a preservative solution, which may intimately contact the tissue samples 26 through the various apertures and passages in the platens 22, 24 and diskette housings 72, 74 noted above. When the devices 20 arrive at the intended destination, such as a cryogenic storage facility, the entire device 20 holding the full tissue sample 26 may be stored, or individual sub-samples 120 housed in diskette assemblies 70 may be separated and stored as needed. If the entire device 20 is cryogenically stored and only a sub-sample 120 is later needed, the device 20 may be thawed and the sub-sample 120 separated without direct handling of the tissue sample 26. Similarly, the device 20 permits an explant culture procedure for stem cell derivation to be performed, and is capable of being immersed in a cryogenic preservation medium and returned to cryogenic storage more than one time without directly handling the tissue sample.

Figure 20:
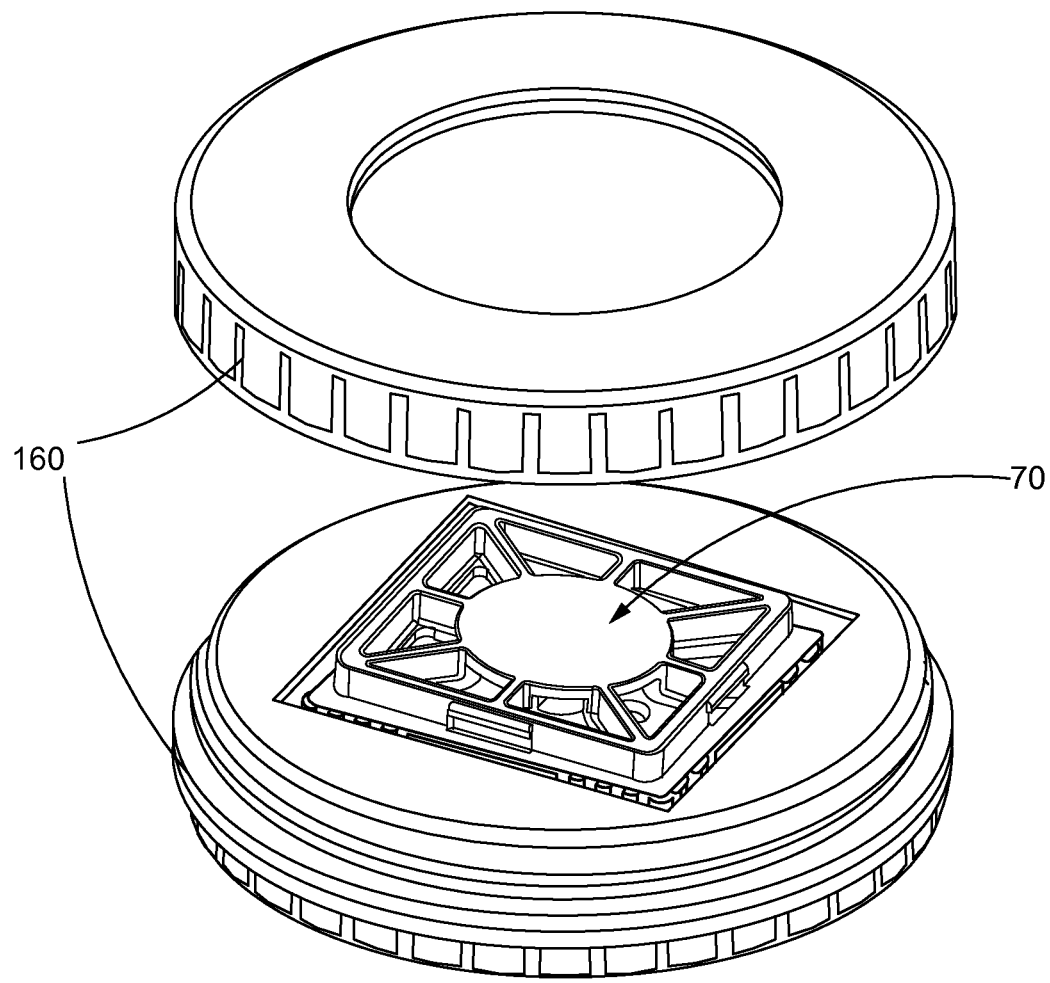
FIG. 20 is an exploded perspective view showing an alternative transport vial for a single diskette assembly.

FIG. 20 illustrates a diskette assembly 70 disposed in an individual cryogenic vial 160. The cryogenic vial 160 may be filled with a preservative solution and prepared for cryogenic storage, thereby allowing individual sub-samples 120 to be separated and stored with minimal handling of the tissue.

INDUSTRIAL APPLICABILITY

The device as described allows a placental tissue sample to be secured, transported in an appropriate protection medium, transferred to an appropriate cryogenic preservation medium and frozen intact. The device further allows, at a future time, a thawing procedure followed by an explant stem cell derivation culture procedure, which upon conclusion allows the return to cryogenic preservation for a second or more times.

The device may be used to capture a tissue sample at a child birthing event; permit immersion in a medium for transportation preservation to the next laboratory site; permit transfer from a transportation medium to a cryo-preservation medium; permit cryogenic storage; permit removal and thawing from cryogenic storage; and permit subsequent explant culturing to derive Mesenchymal-like stem cells, all with minimal or no direct handling of the sample. Furthermore, the device allows the sample to sustain repetitive cycles of cryogenic freezing, thawing, and explant stem cell derivation.

Additionally, portions of the device may be constructed of a biomimetic material that can serve as a tissue scaffold that can be directly utilized after a placental tissue derived Mesenchymal-type stem cell derivation procedure.

In view of the foregoing, the subject matter disclosed herein may facilitate one or more of the following advantages:

(1) Providing a staging platform or work surface upon which to present and stabilize a large and unwieldy tissue sample for further manipulation and preparation. This is accomplished by a rigid bottom platen assembly. Optional detachable legs are offered as a means of additional elevation of the working surface as needed;

(2) After staging, the sample may be secured in a manner that retains flatness and prevents folding, curling, shrinkage or other movement, as the sample will normally tend to migrate in many directions. This is accomplished by mating a rigid top platen assembly over the bottom platen assembly, and having the ability to clamp the two platen halves together, thus capturing the large tissue sample between the halves.

(3) Because a singular large sample may be most conducive to transportation for further professional preservation, the platen assemblies may be configured to permit nested stacking in a compact manner that facilitates insertion into a transport container. Also, because exposure to air should be limited, the large tissue sample may be quickly placed within a preserving liquid solution, and the components comprising the platen assembly may facilitate maximum intimate liquid contact with top and bottom tissue surfaces when the platens are immersed in the solution. Discrete passages may be formed in the surfaces contacting and retaining the tissue sample to promote fluid contact with the tissue sample. In some embodiments, the platen materials in contact with the tissue sample may be formed of a hydrophilic material to maximize surface wetting.

(4) The ability to separate the large tissue sample into multiple sub-samples may provide additional advantages. When tissue samples are cryogenically preserved, a common practice is to thaw the entire tissue sample, extract the desired sub-sample, and then re-freeze the remainder of the tissue sample. Each thaw and freeze cycle is believed to diminish the viability of the sample. Accordingly, it may be advantageous to provide the ability to freeze and thaw smaller pieces of the large sample on a more selective basis, as permitted by the use of the diskette assemblies taught herein.

(5) Similar to transport conditions, when the large tissue sample is transformed into smaller multiple sub-samples for cryogenic storage, the sub-samples are typically immersed in a cryogenic preservation medium. The methods and apparatus disclosed herein promote intimate contact between the surfaces of the tissue sample and the preservation medium.

It will be appreciated that the foregoing description provides examples of the disclosed assembly and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A device for securing a tissue sample, comprising:
   a bottom platen including:
      a bottom platen base defining a bottom platen base inner surface;
      a bottom platen side wall extending upwardly from the bottom platen base, the bottom platen side wall and bottom platen base defining a bottom platen base receptacle;
      a flange coupled to a top of the bottom platen side wall and defining a bottom platen engagement surface spaced from the bottom platen base inner surface, the bottom platen engagement surface being substantially planar and extending around a perimeter of the bottom platen base receptacle; and
      a first alignment structure coupled to the bottom platen side wall; and
   a top platen configured to be separable from the bottom platen, the top platen including:
      a top platen cover defining a top platen cover inner surface;
      a top platen side wall extending downwardly from the top platen cover, the top platen side wall and top platen cover defining a top platen cover receptacle,
      a bottom portion of the top platen side wall defining a top platen engagement surface spaced from the top platen cover inner surface, the top platen engagement surface extending around a perimeter of the top platen cover receptacle and is shaped to cooperatively interact with the bottom platen engagement surface; and
      a second alignment structure coupled to the top platen side wall and configured to engage the first alignment structure, wherein the first and second alignment structures are cooperatively positioned on the respective bottom platen side wall and top platen side wall to substantially align the bottom platen engagement surface with the top platen engagement surface when the first alignment structure engages the second alignment structure, wherein the top platen engagement surface is disposed at a tissue engaging position relative to the bottom platen engagement surface, thereby to engage a perimeter portion of the tissue sample, when the top platen is coupled to the bottom platen.

2. The device of claim 1, further comprising a coupler assembly configured to releasably couple the top and bottom platens.

3. The device of claim 2, in which the coupler assembly comprises a latch rotatably coupled to the top platen and a coupler recess formed in the bottom platen and configured to releasably engage the latch.

4. The device of claim 1, in which the first alignment structure comprises a pair of brackets extending outwardly from the bottom platen side wall and in which the second alignment structure comprises a tab sized for insertion between the pair of brackets.

5. The device of claim 1, in which
   the bottom platen base defines a plurality of bottom platen base apertures fluidly communicating between an exterior of the bottom platen and the bottom platen base receptacle; and
   the top platen cover defines a plurality of top platen cover apertures fluidly communicating between an exterior of the top platen and the top platen cover receptacle.

6. The device of claim 1, in which the top platen engagement surface comprises an edge sufficiently sharp to sever through the tissue sample when the top platen is coupled to the bottom platen.

7. A device for securing a tissue sample, comprising:
   a bottom platen including:
      a bottom platen base defining a bottom platen base inner surface, the bottom platen base inner surface defining an array of bottom platen base recesses, a base retainer coupled to each bottom platen base recess;
      a bottom platen side wall extending upwardly from the bottom platen base, the bottom platen side wall and bottom platen base defining a bottom platen base receptacle; and
      a bottom platen flange coupled to a top of the bottom platen side wall and defining a bottom platen engagement surface spaced from the bottom platen base inner surface, the bottom platen engagement surface being substantially planar and extending around a perimeter of the bottom platen base receptacle; and
   a top platen configured to be separable from the bottom platen, the top platen including:
      a top platen cover defining a top platen cover inner surface;
      an array of cover apertures defined by the top platen cover, each cover aperture being positioned to register with an associated bottom platen base recess, each associated cover aperture and bottom platen base recess defining a diskette receptacle;
      a top platen side wall extending downwardly from the top platen cover, the top platen side wall and top platen cover defining a top platen cover receptacle; and
      a bottom portion of the top platen side wall defining a top platen engagement surface spaced from the top platen cover inner surface, the top platen engagement surface extending around a perimeter of the top platen cover receptacle and is shaped to cooperatively interact with the bottom platen engagement surface;
   a diskette assembly disposed in each diskette receptacle, each diskette assembly including:
      a diskette lower housing including:
         a lower housing base sized for insertion into an associated bottom platen base recess and configured to releasably couple to an associated base retainer of the bottom platen, the lower housing base defining a lower housing base inner surface;
         a lower housing side wall extending upwardly from the lower housing base so that the lower housing base and the lower housing side wall define a lower housing receptacle, a lower housing shoulder formed in the lower housing side wall defining a lower housing engagement surface spaced from the lower housing base inner surface and extending around a perimeter of the lower housing receptacle;
a diskette upper housing including:
an upper housing cover sized for insertion through the cover aperture and configured to releasably couple to the top platen, the upper housing cover defining an upper housing cover inner surface;
an upper housing side wall extending downwardly from the upper housing cover, the upper housing side wall and upper housing cover defining an upper housing receptacle, the upper housing side wall including an upper housing shoulder extending outwardly from the upper housing cover and having a shoulder surface configured to engage the upper housing cover inner surface to prevent insertion of the upper housing shoulder through the cover aperture, the upper housing side wall having a lower edge defining an upper housing engagement surface spaced from the upper housing cover inner surface, the upper housing engagement surface extending around a perimeter of the upper housing receptacle and is shaped to cooperatively interact with the lower housing engagement surface; and
an alignment assembly coupled to the top and bottom platens and configured to substantially align the first and second engagement surfaces as the top platen is coupled to the bottom platen, wherein the cover aperture and associated base recess of each diskette receptacle are cooperatively positioned on the top platen and bottom platen, respectively, to substantially align the upper housing engagement surface and lower housing engagement surface when the top platen is coupled to the bottom platen.

8. The device of claim 7, in which each diskette upper housing is movable between a normal position, in which the diskette upper housing engages the top platen and the upper housing engagement surface is positioned above the top platen engagement surface, and an actuated position, in which the diskette upper housing is disengaged from the top platen and the upper housing engagement surface is positioned below the top platen engagement surface.

9. The device of claim 8, in which the upper housing engagement surface is disposed at a tissue engaging position relative to the lower housing engagement surface when the diskette upper housing is in the actuated position.

10. The device of claim 8, in which the upper housing engagement surface engages the lower housing engagement surface when the diskette upper housing is in the actuated position, and in which the upper housing engagement surface comprises an edge sufficiently sharp to sever through the tissue sample when the diskette upper housing is in the actuated position.

11. The device of claim 8, in which the diskette lower housing is configured to releasably retain the diskette upper housing in the actuated position.

12. The device of claim 11, in which the diskette lower housing further includes a lower housing flange extending inwardly from the lower housing side wall and defining a lower housing flange surface, and in which the diskette upper housing further includes a flexible tab protruding outwardly from the upper housing side wall and defining an upper tab surface, wherein the upper tab surface engages the lower housing flange surface to releasably couple the diskette upper housing to the diskette lower housing when the diskette upper housing is in the actuated position.

13. The device of claim 7, in which the upper housing engagement surface defines a plurality of upper housing engagement surface passages fluidly communicating between an exterior of the diskette upper housing and the upper housing receptacle.

14. The device of claim 7, in which:
the bottom platen base defines a plurality of bottom platen base apertures fluidly communicating between an exterior of the bottom platen and the bottom platen base receptacle;
each upper housing cover defines a plurality of upper housing cover passages fluidly communicating between an exterior of the upper housing cover and the upper housing receptacle; and
each lower housing base defines a plurality of lower housing base apertures fluidly communicating between an exterior of the lower housing base and the lower housing receptacle.

15. The device of claim 7, in which:
the lower housing side wall of each diskette lower housing defines a lower housing side wall periphery; and
the bottom platen base recesses are sufficiently spaced to provide a cutting gap between the lower housing side wall peripheries associated with adjacent diskette lower housings.

16. The device of claim 15, in which the bottom platen further comprises a base platform disposed between adjacent bottom platen base recesses, the base platform defining an upper platform surface aligned with the cutting gap.

17. A diskette assembly for securing a tissue sample, the diskette assembly comprising:
a diskette lower housing including:
a lower housing base defining a lower housing base inner surface;
a lower housing side wall extending upwardly from the lower housing base so that the lower housing base and the lower housing side wall define a lower housing receptacle;
a lower housing shoulder formed in the lower housing side wall defining a lower housing engagement surface spaced from the lower housing base inner surface and extending around a perimeter of the lower housing receptacle; and
a lower housing retainer coupled to the lower housing side wall; and
a diskette upper housing including:
an upper housing cover defining an upper housing cover inner surface;
an upper housing side wall extending downwardly from the upper housing cover, the upper housing side wall and upper housing cover defining an upper housing receptacle, the upper housing side wall having a lower edge defining an upper housing engagement surface spaced from the upper housing cover inner surface, the upper housing engagement surface extending around a perimeter of the upper housing receptacle and shaped to cooperatively interact with the lower housing engagement surface; and
an upper housing retainer coupled to the upper housing side wall and configured to releasably engage the lower housing retainer when the diskette upper housing is inserted into the diskette lower housing;
wherein the upper housing engagement surface is disposed at a tissue engaging position relative to the lower housing engagement surface when the diskette upper housing is inserted into the diskette lower housing.

18. The diskette assembly of claim 17, in which:
the lower housing retainer comprises a lower housing flange extending inwardly from the lower housing side wall and defining a lower housing flange surface; and
the upper housing retainer comprises a flexible tab protruding outwardly from the upper housing side wall and defining an upper tab surface, wherein the upper tab surface engages the lower housing flange surface to releasably couple the diskette upper housing to the diskette lower housing when the diskette upper housing is inserted into the diskette lower housing.

19. The device of claim 17, in which:
each upper housing cover defines a plurality of upper housing cover passages fluidly communicating between an exterior of the upper housing cover and the upper housing receptacle; and
each lower housing base defines a plurality of lower housing base apertures fluidly communicating between an exterior of the lower housing base and the lower housing receptacle.

20. The device of claim 17, in which the upper housing engagement surface defines a plurality of upper housing engagement surface passages fluidly communicating between an exterior of the diskette upper housing and the upper housing receptacle.

* * * * *